United States Patent [19]

Desjardins et al.

[11] Patent Number: 4,825,263
[45] Date of Patent: Apr. 25, 1989

[54] OPTICAL METHOD AND APPARATUS FOR DETERMINING THREE-DIMENSIONAL CHANGES IN FACIAL CONTOURS

[75] Inventors: Paul J. Desjardins, Maplewood; Stanley M. Dunn, Belle Mead; Maano Milles, Berkeley Heights, all of N.J.

[73] Assignees: University of Medicine & Dentistry of New Jersey, Newark; Rutgers University, Piscataway, both of N.J.

[21] Appl. No.: 57,577

[22] Filed: Jun. 2, 1987

[51] Int. Cl.[4] ............................................. G01B 11/24
[52] U.S. Cl. .................................................... 356/376
[58] Field of Search ......................... 356/376; 382/2, 6

[56] References Cited

U.S. PATENT DOCUMENTS

| | | | |
|---|---|---|---|
| 3,762,818 | 10/1973 | Johnson et al. | 356/376 |
| 3,814,521 | 6/1974 | Free | 356/376 |
| 3,952,150 | 4/1976 | Gerardia et al. | 356/376 |
| 4,644,583 | 2/1987 | Watanabe et al. | 356/376 |
| 4,657,394 | 4/1987 | Haliova | 356/376 |

Primary Examiner—Thomas H. Tarcza
Assistant Examiner—Ian J. Lobo
Attorney, Agent, or Firm—Klauber & Jackson

[57] ABSTRACT

A method of optically mapping a person's face includes the steps of illuminating the face through a grid structure to produce a grid representation on the face; viewing the illuminated face with a video camera; producing a video signal in response to the step of viewing; converting the video signal to digital form; storing a frame of the digitized video signal in a frame memory; defining the grid representation on the face, from the stored video signal; locating coordinates of the intersection points of the grid representation; determining curvatures of the grid representation at the located intersection points; and three-dimensionally reconstructing the surface of the face from the coordinates and curvatures of the intersection points.

6 Claims, 7 Drawing Sheets

FIG. 7
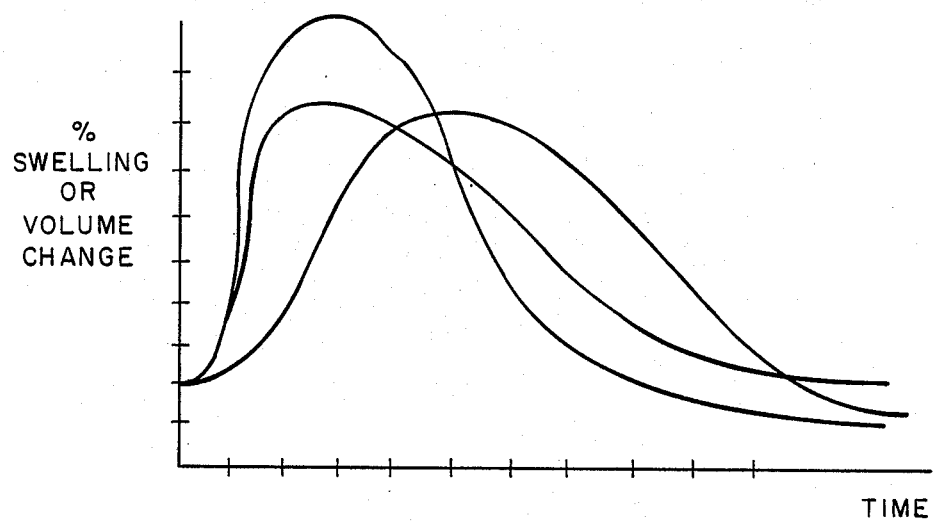
% SWELLING OR VOLUME CHANGE
TIME
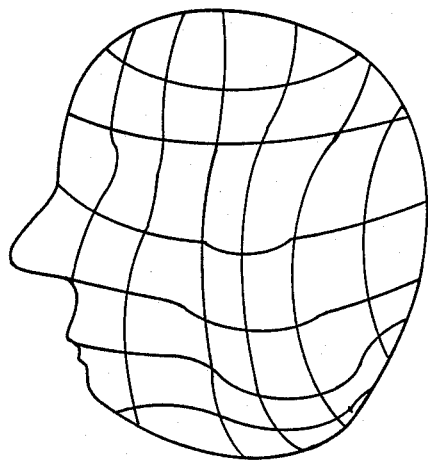
FIG. 8

OPTICAL METHOD AND APPARATUS FOR DETERMINING THREE-DIMENSIONAL CHANGES IN FACIAL CONTOURS

BACKGROUND OF THE INVENTION

The following invention relates generally to a method and apparatus for determining three-dimensional changes in a surface, and more particularly, is directed to a method and apparatus for optically determining three-dimensional changes in facial contours due to swelling and the like. In many instances, it is necessary to measure three-dimensional changes in facial contours. For example, the surgical extraction of impacted wisdom teeth is followed almost invariably by some degree of post-operative swelling of the related soft tissues. Various anti-inflamatory drugs have been utilized for reducing such swelling. In order to assess the anti-inflamatory effects of these drugs, it is necessary 15 to measure the extent that the swelling is reduced over a period of time. However, one of the major difficulties in investigations of facial swelling is that of accurately measuring the swelling. With the measuring techniques utilized to date, pre-operative and post-operative measurements are taken and the results are compared to obtain an indication of the extent of swelling.

Several measurement techniques have been employed to assess swelling following surgery, including stereophotogrammetry and contrast radiography. The stereophotogrammetric technique is disclosed in an article, D. A. Dixon et al., "Minimal Forms of the Cleft Syndrome Demonstrated by Stereophotogrammetric Surveys of the Face", British Dental Journal, Mar. 7, 1972, pgs. 183-189. In addition to the above techniques, clinical analysis, that is, observation of the patient, has also been utilized to determine the extent of swelling. William B. Linnenberg "The Clinical Evaluation of Dexamethasone in Oral Surgery", Oral Surgery, Oral Medicine and Oral Pathology, Vol. 20, No. 1, 1965, pgs. 6-28.

Still further, mechanical techniques for measurement of swelling have been utilized. For example, with one mechanical method, one arm of a pair of callipers is placed in the interdental space between the mandibular first and second molars and the other arm of the callipers is placed in light contact with the external cheek surface. J. H. Sowray, "An Assessment of the Value of Lyophilised Chymotrypsin in the Reduction of Post-Operative Swelling Following the Removal of Impacted Wisdom Teeth", British Dental Journal, Feb. 21, 1961, pgs. 130-133. However, utilization of callipers does not provide an accurate measurement of the extent of swelling since such measurement is taken at a single point on the cheek. A similar mechanical technique is described in the article "An Investigation into Some of the Factors Concerned in the Surgical Removal of the Impacted Lower Wisdom Tooth including a Double-Blind Trial of Chymoral", by Ian W. Cameron, published in the British Journal of Oral Surgery (1980) 18, pgs. 112-124. However, as recognized on page 21 of this article, the device used therein is only capable of measuring the maximum lateral extension of the swelling of the cheek. It is noted that the latter article at page 121 indicates that a volume measurement would be a true measure of post-operative oedema, but further indicates that no such measurement seems possible unless using a very sophisticated stereophotogrammetric technique. Another mechanical technique that has been utilized is described in the article, P. Lokken, "Bilateral Surgical Removal of Impact Lower Third Molar Teeth as a Model for Drug Evaluation: A test for Ibuprofen", Europ. J. Clin. Pharmacol. 8, pgs. 209-216, 1975. The device of this latter article consists of 16 adjustable plastic screws, eight on each side of the face, on bilateral plates, which are fixed on a facial bow attached to an individual bite-block. The plastic screws are adjusted into touching contact with the skin and are adjusted at each sitting and then compared with pre-operative measurements to give an indication of swelling. However, again, with this device, only point measurements are taken.

In an article entitled "Capturing Facial Surface Information", Photogrammetric Engineering and Remote Sensing, Vol. 52, No. 9, Sept., 1986, pps. 1539-1548, by Keefe and Riley, there is disclosed a manner of mapping a facial surface by projecting a laser light onto the surface and using two cameras to obtain a stereo image. The system automatically digitizes the information using an image analyzer and the system's computer base provides a graphic manipulation of the resulting surface data for use in studying the facial surface. However, this method is disadvantageous since it requires a collimated or laser light source and two cameras.

In an article "Moveable Light-Stripe Sensor For Obtaining Three-Dimensional Coordinate Measurements", SPIE, Volume 360, pps. 326-333, by Agin and Highnam, there is disclosed an apparatus for obtaining three-dimensional surface information that may be used to recognize objects and determine their position and orientation. A lightweight camera and a light-stripe projector using an infrared laser diode are mounted in the hand of a robot manipulator. Image-processing routines locate the stripe in the camera image, and homogeneous coordinate transform techniques are then applied to solve for the three-dimensional coordinates of points illuminated by the stripe. However, this method and apparatus is also relatively complex and difficult to use.

Other references which may be relevant to the present invention include the following:

An article entitled "Ultrasonic Pulse-Echo Measurements in Teeth", Arch: Oral Bio, by Barber, Lees and Lobene, Vol. 4, pps. 745-760, 1969, Pergamon Press, printed in Great Britain; an Article entitled "A Photogrammetric Method Of Measuring The Volume Of Facial Swellings", from the Department of Oral Surgery State Dental School, Malmo and the Department of Photogrammetry, Royal Institute of Technology, Stockholm, Sweden, 1953, by Bjorn, Lundqvist and Hjelmstrom; an article entitled "Stereophotogrammetric Measurement of Normal Facial Asymmetry in Children", pps. 536-548, by P. H. Burke; an article entitled "A Photographic Method of Assessing Swelling Following Third Molar Removal", Int. J. Oral Surg. by Gool, Bosch and Boering, Vol. 4, pps. 121-129, 1975; an article entitled "Noncontact Visual Three-Dimensional Ranging Devices", SPIE, Vol. 283, 3-D Machine Perception, pps. 48-53, (1981), an article entitled "The Facial Plethysmograph: A New Instrument To Measure Facial Swelling Volumetrically", J. Oral Maxillofac Surg., Vol. 43, pps. 346-352, 1985, by Milles, Desjardins and Pawel; an article entitled "The Measurement And Use of Registered Reflectance and Range Data in Scene Analysis", Proceedings of the IEEE, Vol. 65 No. 2, February, 1977, pps. 206-220, by Nitzan, Brain and Duda; an article entitled "Generating Models of Solid Objects by Matching 3D Surface Segments", proceedings of the 8th International Joint Conference on Artificial Intelligence, West Germany, Aug. 8–12, 1983, by M. Potmesil; an article entitled "Trypsin in the Treatment of Swellings of the Head and Neck", American Journal of Surgery, Vol. 96, December, 1958, pps. 787–791, Stuteville, et al.; an article entitled "Regular Pattern Projection For Surface Measurement" from Robotics Research, The Second International Symposium, MIT Press 1985, by Sugihara, et als.; an article entitled "Describing Surfaces" from Robotics Research, The Second International Symposium, MIT Press by M. Brady, et al.; and an article entitled "Minimal Forms of the Cleft Syndrome Demonstrated by Stereophotogrammetric Surveys of the Face", Brit. Dent. J., by D.A. Dixon et al., pgs. 183–189, 1972.

In addition, the following U.S. patents generally describe mapping of three-dimensional surfaces or relate similarly thereto as follows:

U.S. Pat. Nos. 3,805,238; 3,884,577; 4,055,833; 4,091,415; 4,109,237; 4,414,546; 4,468,807; 4,573,193; 4,620,318; and 4,641,349. However, these patents generally describe apparatus and methods which attempt to map three-dimensional surfaces absolutely, that is, without any known reference frame. This renders the methods and apparatus relatively complex and cumbersome to use.

OBJECTS AND SUMMARY OF THE INVENTION

Accordingly, it is an object of the present invention to provide a method and apparatus for optically measuring a volume change in facial swelling of a person.

It is another object of the present invention to provide a method and apparatus for optically measuring volume changes in the facial swelling of a person by mapping a grid representation onto the person's face.

In accordance with an aspect of the present invention, a method of optically mapping a three-dimensional surface, includes the steps of illuminating the surface through a grid structure to produce a grid representation on the suraface; viewing the illuminated surface with a video camera; producing a video signal in response to the step of viewing; converting the video signal to digital form; storing a frame of the digitized video signal in a frame memory; defining the grid representation on the surface from the stored video signal; locating coordinates of the intersection points of the grid representation; determining curvatures of the grid representation at the located intersection points; and three-dimensionally reconstructing the surface from the coordinates and curvatures of the intersection points.

In accordance with another aspect of the present invention, apparatus for optically mapping a three-dimensional surface includes illumination means for illuminating the surface through a grid structure to produce a grid representation on the surface; video camera means for viewing the illuminated surface and for producing a video signal in response thereto; analog-to-digital converting means for converting the video signal to digital form; memory means for storing a frame of the digitized video signal in a frame memory; and central processing means for defining the grid representation on the surface from the stored video signal, for locating coordinates of the intersection points of the grid representation, for determining curvatures of the grid representation at the located intersection points, and for three-dimensionally reconstructing the surface from the coordinates and curvatures of the intersection points.

The above and other objects, features and advantages of the present invention will become readily apparent from the following detailed description thereof which is to be read in connection with the accompanying drawings.

BRIEF DESCRIPTION OF THE DRAWINGS

FIG. 7 is a graphical representation of volume change versus time, obtained with the present invention; and FIG. 8 is a schematic representation of the person's face, reconstructed with the present invention.

DETAILED DESCRIPTION OF A PREFERRED EMBODIMENT

Figure 1:
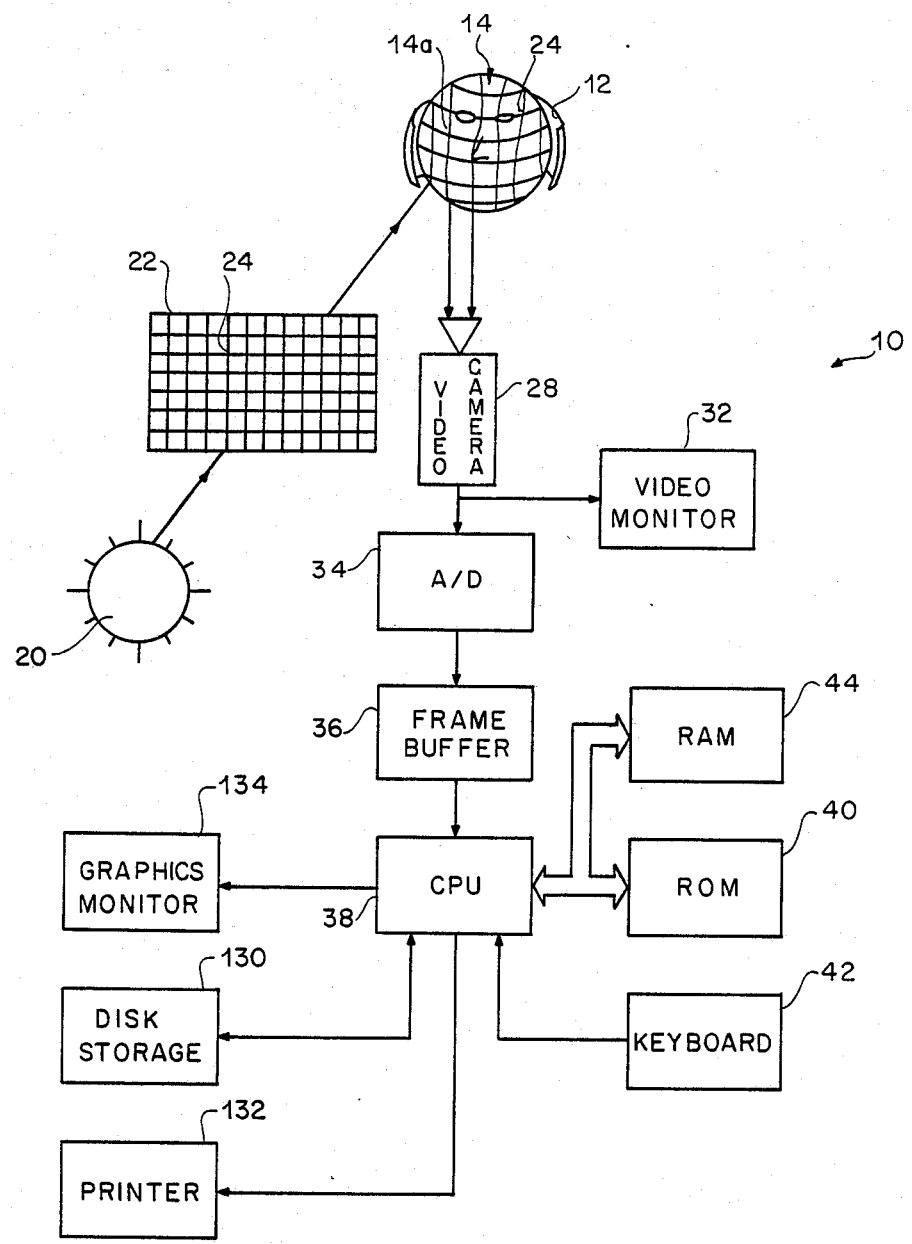
FIG. 1 is a schematic, block diagram of the overall apparatus for optically determining three-dimensional changes in facial contours according to the present invention.
Figure 2:
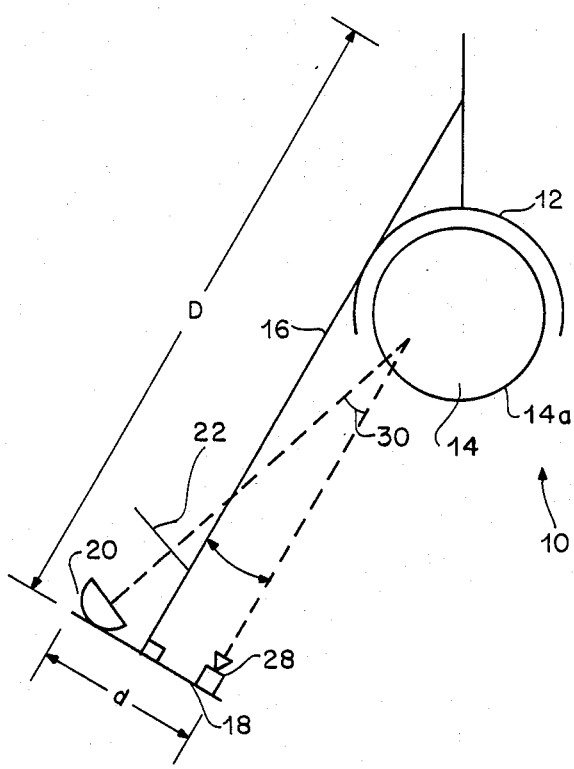
FIG. 2 is a schematic, top plan view of the mechanical portion of the apparatus of FIG. 1.

Referring to the drawings in detail, and initially to FIGS. 1 and 2 thereof, apparatus 10 for optically measuring three-dimensional changes in facial contours according to the present invention includes a restraint device 12 of a conventional nature which restrains the person's head 14 from moving so as to provide a fixed reference thereof. An arm 16 is attached to restraint device 12 for rotation about head 14, the free end of arm 16 having a support 18 secure perpendicularly thereto. A structured light source 20, such as an ordinary incandescent light bulb, is mounted to support 18 for illuminating face 14a of the patient.

In accordance with the present invention, a translucent or transparent plate 22 having a grid structure 24 thereon is mounted in front of light source 20, and for example, can be secured to arm 16. For example, plate 22 can be a translucent plate having a grid structure 24 etched thereon, a photographic plate or the like. Thus, light rays from light source 20 pass through plate 22 and illuminate the patient's face 14a. Because of grid structure 24, a grid pattern or representation 24 is projected on the patient's face 14a.

A video camera 28 is also mounted on support 18 as close as possible to light source 20 for viewing the illuminated patient's face 14a. Ideally, light source 20 and video camera 28 should be attached at the same point. However, since this is not possible, the angle of incidence 30, that is, the angle made by the light travelling from light source 20 to the person's face 14a and then to video camera 28, is made as small as possible. In this regard, the distance d between light source 20 and video camera 28 is much smaller than the distance D from support 18 to the point of attachment of arm 16 to restraint device 12, as shown in FIG. 2.

Video camera 28 produces a resultant analog video signal which is supplied to a video monitor 32 for displaying the patient's head 14 and face 14a thereon. More importantly, the analog video signal is used for processing in accordance with the present invention to determine three-dimensional changes in facial contours.

Specifically, the analog video signal from video camera 28 is supplied to an analog-to-digital (A/D) converter 34 where it is converted to digital form. The digitized signal from A/D converter 34 is then supplied to a frame buffer 36 which stores one freeze frame of the video picture displayed on video monitor 32. The digitized video signal from frame buffer 36 is then supplied to a central processing unit (CPU) 38 for further processing in accordance with appropriate software stored in a read only memory (ROM) 40 and instructions from a keyboard 42. In addition, a random access memory (RAM) 44 is connected with CPU 38 for providing a work area for operations to be performed by CPU 38.

Figure 3:
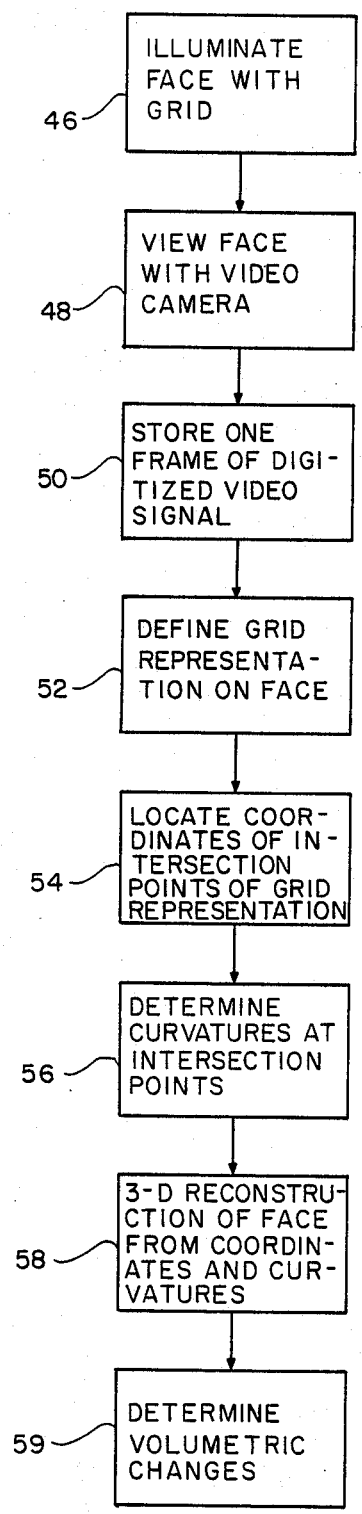
FIG. 3 is an overall flow chart diagram of the method of using the apparatus of FIG. 1.

Referring now to FIG. 3, an overall flow chart diagram which describes the different processes according to the present invention starts with illumination of face 14a with grid structure 24 to provide the aforementioned grid pattern 26, in step 46. Thereafter, face 14a is viewed with video camera 28 in step 48 and the video signal is then digitized and one frame thereof is stored in frame buffer 36, as indicated in step 50 of FIG. 3. It will be appreciated that the digitized video signal stored in frame buffer 36 includes information regarding the entire face, including grid pattern or representation 26 thereon. Accordingly, in step 52, it is necessary to isolate the grid pattern or representation 26 from the remainder of the video information, that is, to define only the grid representation on face 14a. In the next step 54, it is necessary to locate the coordinates of intersection points of grid representation 26, that is, the points where the horizontal and vertical lines of grid representation 26 intersect, and to thereafter determine curvatures of face 14a at such intersection points in step 56. In step 58, there is a three-dimensional reconstruction of face 14a from the coordinates of the intersection points of grid representation 26 and curvatures of face 14a at such points. Then, volumetric changes in the face due to, for example, swelling, are determined in step 59.

Figures 4A, 4B:
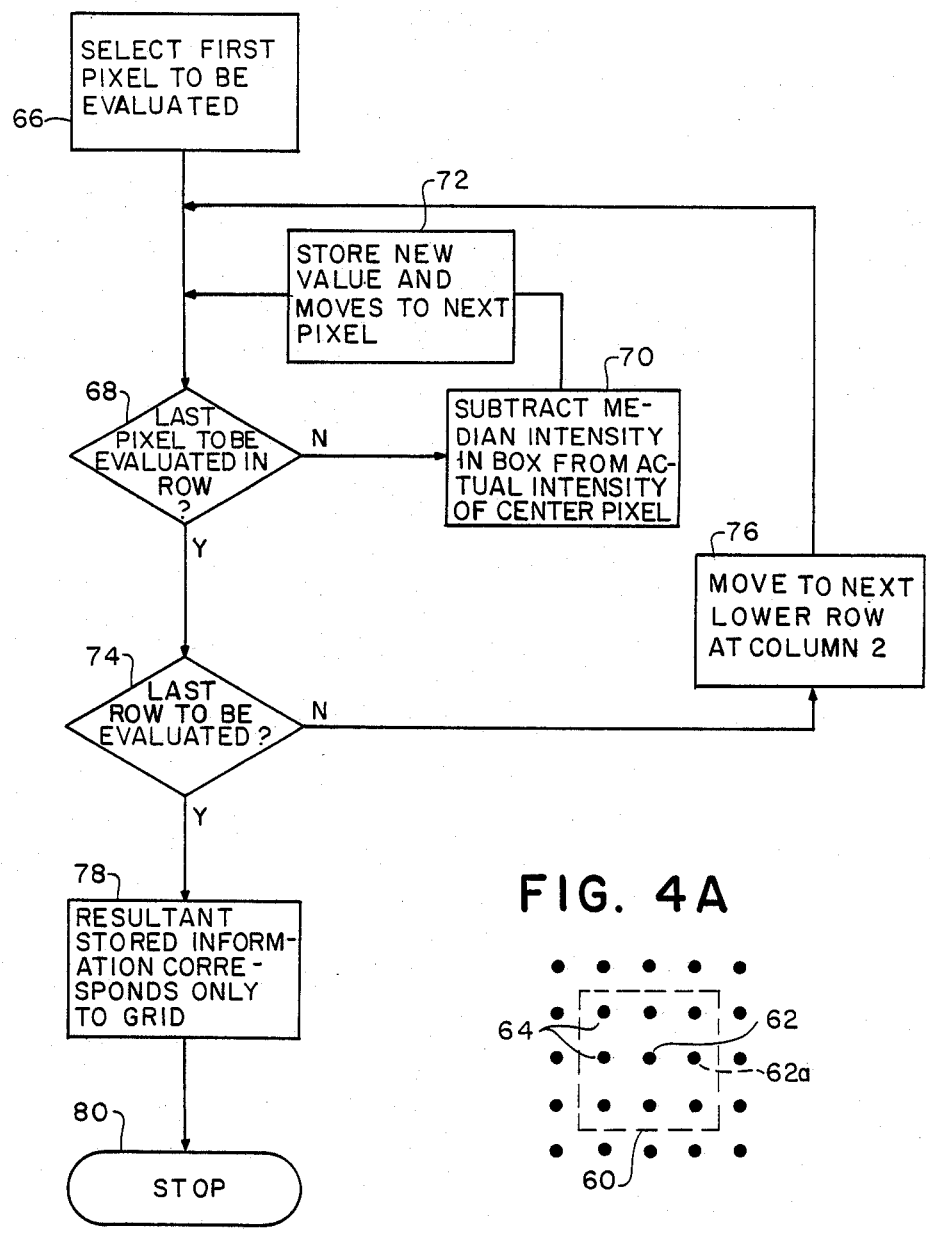
FIG. 4A is a schematic diagram of a plurality of pixels and an imaginary box constructed therearound for isolating the grid representation.
FIG. 4B is a flow chart diagram explaining how the grid representation on the person's face is defined.

Referring specifically to FIG. 4B, there is shown a flow chart diagram for defining grid representation 26 on face 14a. As is well known, video information is represented by a plurality of pixels. Thus, broadly speaking, the step of defining grid representation 26 on face 14a is accomplished by using a median filter, whereby the values of light intensity in an imaginary box surrounding each pixel is subtracted from the light intensity value of the particular pixel which is surrounded thereby.

More specifically, and referring first to FIG. 4A, an imaginary box 60 is constructed around a center pixel 62. For example, as shown, imaginary box 60 can be constructed of a matrix of $3 \times 3$ pixels 64. The light intensity values of all of pixels 62 and 64 in imaginary box 60 is determined, and these light intensity values are averaged to determine a median light intensity for imaginary box 60. This median light intensity value is then subtracted from the actual light intensity value of center pixel 62 about which imaginary box 60 was constructed. This operation is performed for each pixel about which such a box 60 can be constructed, that is, practically speaking, 95% of all pixels on the video picture of face 14a, whereupon the resultant light intensity values define only grid representation or pattern 26 on face 14a.

More specifically, and referring to FIG. 4B, the first point or pixel is selected or initialized for processing in step 66. In accordance with the present method, this pixel is generally selected in the second row of the second column of the video picture. The reason that the first row or the first column is not selected is that a $3 \times 3$ matrix of pixels cannot be constructed about such a point. Generally, in accordance with the present method, the order for determining the selection of pixels starts at the upper left corner of the video picture and moves rightwardly along each row. When the last pixel to be evaluated in each row is obtained, the process moves to the second column of the next lower row and so on until the last pixel at the lower right corner of the video picture is evaluated. Thus, after the first pixel is selected, it is determined in step 68 whether this pixel is the last pixel to be evaluated in the row. If not, the process moves to step 70, where the process described in FIG. 4A is performed. Specifically, in step 70, imaginary box 60 is constructed about the selected pixel 62 and the median light intensity of the pixels in box 60 is determined and subtracted from the actual light intensity of the center pixel 62. Then, in step 72, this new value for center pixel 62 is stored in RAM 44 and the process moves to the next pixel, for example, pixel 62a shown in FIG. 4A. Then, the process moves back to step 68 to determine if this is the last pixel to be evaluated in the row, and so on.

Figure 5A:
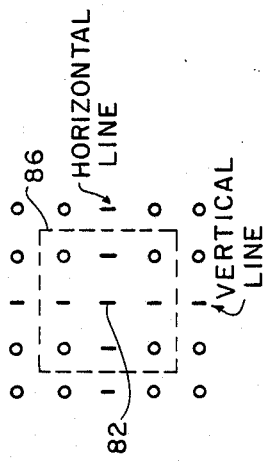
FIG. 5A is a schematic diagram of a plurality of pixels and an imaginary box constructed therearound used for locating intersection points of the grid representation.

If the last pixel to be evaluated in any given row is obtained, the process moves to step 74 where it is determined whether the last row to be evaluated has been reached, which is the next to last row in the actual picture, since a $3 \times 3$ matrix of pixels must be able to be constructed about each pixel. If the last row to be evaluated is not yet obtained, the process moves to step 76 where evaluation is moved to the next lower row at column 2, and then back to step 68. In this manner, each of the pixels in the second row are evaluated one at a time, moving from left to right. Then, the pixels in the next lower row are evaluated, one at a time, moving from left to right, and so on until the last row to be evaluated is completed. At such time, the process moves to step 78, whereby the resultant stored information of the median removed intensities corresponds to a map of the intensities of grid representation 26 only, whereupon this part of the process is stopped at step 80. Once only the light intensities of grid pattern 26 remain, the next step in the process is to locate the intersections of grid pattern 26, that is, where the horizontal and vertical lines of grid pattern 26 intersect. Specifically, if it is assumed that the horizontal and vertical grid lines of grid pattern 26 have an intensity of logic level "1" and all other points have an intensity of logicl level "0", it is only necessary to detect the pattern shown in FIG. 5A. In FIG. 5A, the intersection point is represented by numeral 82, that is, where the horizontal and vertical lines meet.

Figure 5B:
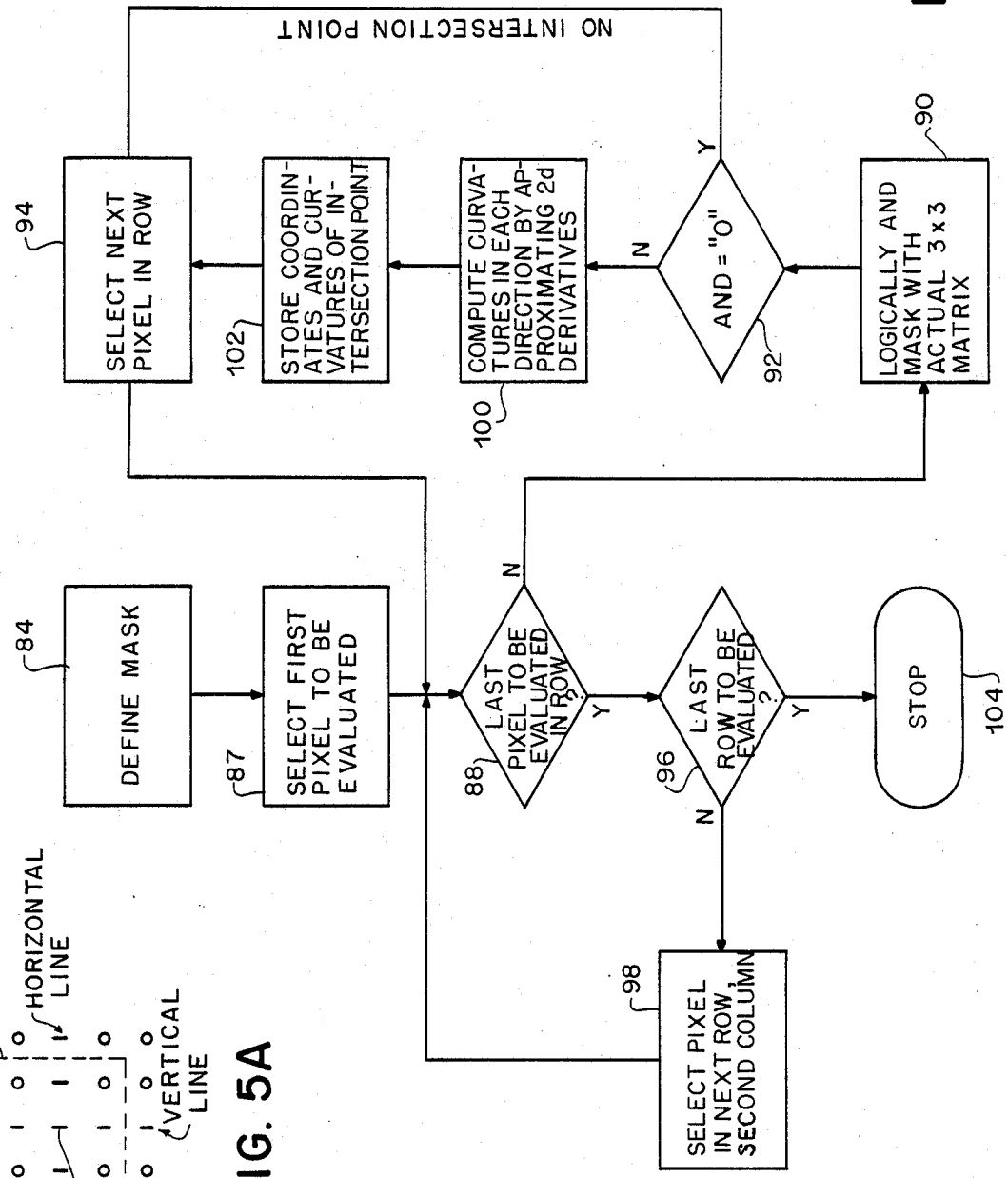
FIG. 5B is a flow chart diagram showing the location of coordinates and the determination of curvatures of the intersection points of the grid representation.

In accordance with the sub-process of FIG. 5B, all intersection points 82 of grid pattern 26 are detected and the curvatures along the horizontal and vertical lines through such intersection points 82 are also determined. Specifically, referring to FIG. 5B, with respect to grid pattern 26 which was isolated in the process of FIG. 4B, a mask is first defined in step 84. The mask can be formed by constructing an imaginary box 86 about a 3×3 matrix of pixels of grid pattern 26 shown in FIG. 5A. Then, with respect to the pixels in grid pattern 26, the first pixel in such grid pattern 26 to be evaluated is selected in step 87. In the same manner as was done in FIG. 4B, each pixel of grid pattern 26 is evaluated, starting from the first selected pixel, which is the pixel in the second row, second column. Thereafter, the pixels are evaluated one at a time, moving rightwardly in the second row. It is then determined whether this is the last pixel to be evaluated in the row in step 88. If not, the process moves to step 90 where a logical AND operation is performed with the mask pattern defined within imaginary box 86 and an actual 3×3 matrix of pixels constructed around the pixel to be evaluated. If the logical AND operation produces a logic level "1" output, this indicates that the pixel to be evaluated is an intersection point and if the logical AND operation produces a logic level "0" output, this indicates that no intersection point has been found.

If no intersection point has been found, as determined in step 92, that is, AND="0", the process moves to step 94 where the next pixel in the row is selected for evaluation and the process moves back to step 88 to determine whether this is the last pixel to be evaluated in the row. If, in step 88, it is determined that this is the last pixel in the row to be evaluated, the process moves to step 96 where it is questioned whether this is also the last row to be evaluated, that is, whether this is the last pixel in the last row to be evaluated. If not, the process moves to step 98 where the pixel in the second column of the next row is selected for evaluation, and the process returns to step 88.

With the process so far described in FIG. 5B, each of the intersection points 82 of grid pattern or representation 26 can be detected in steps 90 and 92 so that the coordinates of such intersection points are known.

Returning back to step 92, if an intersection point is found in such step, that is, AND="1", the curvatures of such intersection point 82 must then be found in the horizontal and vertical directions, that is, along the horizontal and vertical lines of grid pattern or representation 26. Specifically, it must be remembered that grid pattern 26 is focused on the patient's face 14a, and therefore has a curvature associated therewith. Thus, once an intersection point is detected in step 92, the process moves to step 100, where the curvatures of the horizontal and vertical lines passing through the detected intersection point 82 are computed by numerically approximating the second derivatives along each direction at such intersection point 82. This is accomplished by using a sum and difference of the position of points, which is a well known procedure.

Specifically, this second derivative approach is described in the book Numerical Methods, by G. Dahlquist and A. Bjorck, Section 7.5, Pages 307-310, Prentice-Hall, Inc., 1974. More specifically, the following equation found on Page 310 of such book is used:

$$f'_0 \approx \frac{f_1 - f_{-1}}{2h} + \frac{1}{3}\left(\frac{f_1 - f_{-1}}{2h} - \frac{f_2 - f_{-2}}{4h}\right) \quad (1)$$

More specifically, to find the curvature, for example, in the horizontal direction about an intersection point $f_0$, the two intersection points $f_1$ and $f_2$ to the right of intersection point $f_0$ and the two intersection points $f_{-1}$ and $f_{-2}$ immediately to the left of intersection point $f_0$ are used in the above equation. As a result, the first derivative $f_0'$ at the intersection point $f_0$ is found and corresponds to the slope of the horizontal line passing through such intersection point $f_0$. This is performed for each of the intersection points, that is, intersection points $f_0$, $f_1$, $f_2$, $f_{-1}$, $f_{-2}$ and so on to obtain the slopes at each of such intersection points. Then, using the same equation, represented below as follows:

$$f''_0 \approx \frac{f'_1 - f'_{-1}}{2h} + \frac{1}{3}\left(\frac{f'_1 - f'_{-1}}{2h} - \frac{f'_2 - f'_{-2}}{4h}\right) \quad (2)$$

the slopes $f'_1$, $f'_2$, $f'_{-1}$ and $f'_{-2}$ are substituted into the above equation (2) to obtain the curvature $f''_0$ at intersection point $f_0$. In this manner, the curvature of the horizontal and vertical lines through each intersection point can be found. Of course, although the above formulae only use four intersection points about a center intersection point $f_0$ to determine the curvatures at such intersection point, such equations can and are preferably expanded to include more than four intersection points to obtain a more valid representation of the curvatures in the horizontal and vertical directions through the selected intersection point.

Thus, it will be appreciated that previously, imaginary boxes have been constructed about each pixel, each imaginary box being relatively small and comprising, for example a 3×3 matrix of pixels. However, in computing the curvatures, it will be appreciated that there is little curvature in a 3×3 matrix of pixels. Therefore, a larger matrix of pixels is selected about each detected intersection point. For example, a 12×12 matrix of intersection point pixels can be selected. Therefore, once step 100 is completed, the coordinates and curvatures of each intersection point of grid pattern or representation 26 are known and are stored in RAM 44 in step 102. Thereafter, the process returns to step 94 where the next pixel in the row to be evaluated is selected. This continues, as aforesaid, until the last pixel to be evaluated, that is, the pixel in the last column and last row to be evaluated is obtained, whereupon this portion of the process stops in step 104.

Thus, FIG. 5B corresponds to steps 54 and 56 of FIG. 3 whereby the coordinates of the intersection points 82 of grid representation 26 are located and curvatures at such intersection points 82 are determined.

It is then necessary to provide a three-dimensional reconstruction of face 14a from such coordinates and curvatures, as previously indicated with respect to step 58 of FIG. 3.

Figure 6B:
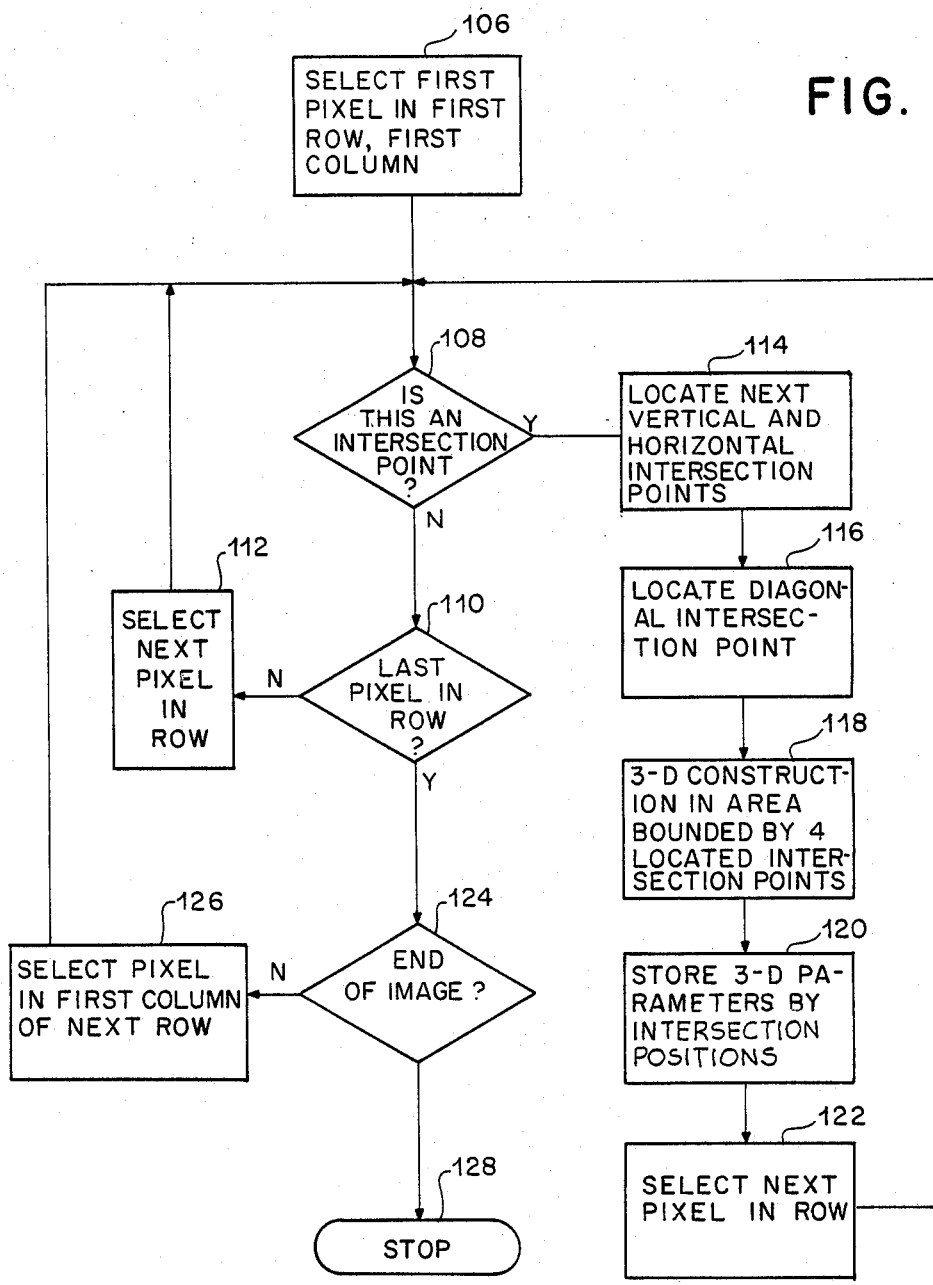
FIG. 6B is flow chart diagram, showing how the face is three-dimensionally reconstructed from the coordinates and curvatures of the intersection points.
Figure 6A:
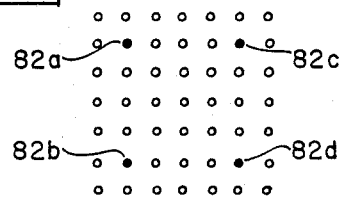
FIG. 6A is a schematic diagram of a plurality of pixels used for performing a three-dimensional construction in the area bounded by four intersection points.

Specifically, referring to FIG. 6A, for each detected intersection point 82a, three other intersection points 82b, 82c and 82d are found so as to form a four pixel matrix of intersection points 82a-82d. From these intersection points, and specifically, from the coordinates and curvatures of such intersection points, the surface parameters of face 14a in such four pixel matrix can be estimated in a well known manner using a least squares procedure. This is performed for each four pixel matrix of intersection points 82 until the entire face 14a is mapped out to obtain a three-dimensional reconstruction thereof.

As shown in FIG. 6B, in step 106, the first pixel in the first row and first column of grid pattern 26 is selected for evaluation. The process then moves to step 108 to determine whether this pixel is an intersection point. If not, the process moves to step 110 to determine whether this pixel is the last pixel in the row. If not, the process moves to step 112, where the next right-most pixel in the row is selected, whereupon the process returns to step 108 to determine whether this new pixel is an intersection point. This continues until an intersection point is detected, such as intersection point 82a in FIG. 6A.

Once intersection point 82a is located, intersection points 82b and 82c below and to the right of intersection point 82a are located in step 114. In the next step 116, intersection point 82d is located which is necessary to construct the four pixel square matrix of intersection points shown in FIG. 6A. This is accomplished by performing two linear searches from intersection points 82b and 82c. Thus, after step 116, all four intersection points 82a-82d have been located. Using the x and y coordinates of the four intersection points 82a-82d and their curvatures, the surface parameters of face 14a in the area bounded by such intersection points can be estimated in a well known manner using a least squares procedure in step 118.

Specifically, the least squares procedure that can be used is described in Technical Report CRL-58, "Computer Descriptions of Curved-Surface Objects From Multiple Projected Pattern Images" prepared for National Science Foundation, Engineering Division, Automation, Bio-Engineering and Sensing Systems under Grant Nos. ENG 76-02488, by M. Potmesil and H. Freeman, of Rensselaer Polytechnic Institute of Troy, N.Y., June, 1978. In accordance with the description therein, the following matrix equation is used to determine the three-dimensional surface parameters:

$$\begin{bmatrix} u_1^3 & u_1^2 & u_1 & 1 \\ u_2^3 & u_2^2 & u_2 & 1 \\ u_3^3 & u_3^2 & u_3 & 1 \\ u_4^3 & u_4^2 & u_4 & 1 \end{bmatrix} \begin{bmatrix} a_x \\ b_x \\ c_x \\ d_x \end{bmatrix} = \begin{bmatrix} X_1 \\ X_2 \\ X_3 \\ X_4 \end{bmatrix} \quad (3)$$

In this matrix equation, $a_x$–$d_x$ are the surface parameters to be determined and are used in the following polynomial equation:

$$a_x X^3 + b_x X^2 + c_x X + d_x = 0 \ldots \quad (4)$$

With this equation, the position of any point along the surface of any four intersection point matrix (FIG. 6A) can be obtained. Such positional information, by solving this equation, provides information as to the three-dimensional characteristics of the facial surface.

To solve the above matrix equation for the surface parameters $a_x$–$d_x$, intersection points 82a, 82c, 82d and 82b are used and the coordinates $X_1$–$X_4$ of such intersection points are inserted into the above matrix equation. It is also necessary to insert the values $u_1$–$u_4$ for each of the intersection points 82a–82d respectively, into the matrix equation and to also provide the square (for example, $u^2 1$) and the cube, (for example $u^3 1$) therein.

Specifically, we assume that the distance along the curvature path from intersection points 82a ($X_1$) to 82c ($X_2$) to 82d ($X_3$) to 82b ($X_4$) is equal to unity, that is, is equal to 1. Thus, the distance $u_4$ from intersection point 82a to intersection point 82b along the aforementioned path is equal to 1, that is, $u_4=1$. In like manner, intersection point 82a ($X_1$) is at the origin, and therefore, $u_1=0$. It is therefore necessary to then determine the distance along the path to intersection points 82c ($X_2$) and 82d ($X_3$). The distance $u_2$ is obtained by performing a double integration of the curvature along the path from intersection point 82a ($X_1$) to intersection point 82c ($X_2$). It is first assumed that, since this distance is relatively small, that the curvature along this path is relatively constant, and accordingly, it is assumed that the curvature along the path is the value of the horizontal curvature previously obtained at intersection point 82a. When this curvature is integrated, the slope of the line at intersection point 82a is obtained and by further integrating the slope of the line, an incremental distance along the curved path is obtained. This is accomplished by the following formula found at Page 293 of the aforementioned book entitled Numerical Methods:

$$I_k = h(\tfrac{1}{2}f2i\text{-}2 + f2i\text{-}1 + \tfrac{1}{2}f2i) + 1/3 \ (\text{-}\tfrac{1}{2}f2i\text{-}2 + f2i\text{-}1 - \tfrac{1}{2}f2i\})$$

The first application of formula (5) uses the curvatures and the second application uses the slopes, and h is an arbitrary constant which is set equal to an estimated spacing moved each time.

Accordingly, the point u is moved along the path from intersection point 82a by this incremental distance. It is then questioned whether this point u is at the second intersection point 82c ($X_2$). If not, another incremental distance is added, and so on. The sum of all of such incremental distances until point 82c is obtained, represents the actual distance along the curved path along intersection point 82a to intersection point 82c. It will be appreciated that this is the actual distance along the curved path and not the straight line distance between these two points. A similar operation is performed for the actual distance between intersection points 82c and 82d and the actual distance between intersection points 82d and 82b. Then, the entire actual distance along the path from intersection points 82a, 82c, 82d and 82b are summed to obtain the actual distance along the entire path. The actual distance between intersection points 82a ($X_1$) and 82c ($X_2$), previously obtained is divided by the distance along the entire path to normalize the same and to obtain the value $u_2$, that is, $u_2=(X_2-X_1)(X_4-X_1)$. In like manner, the value $u_3$ is obtained as follows: $u_3=(X_3-X_1)/X_4-X_1)$, where the differences between intersection points are taken along the actual curved paths.

Therefore, since the values $u_1-u_4$ and $X_1-X_4$ are obtained, the surface parameter values $a_x-d_x$ can be obtained from the above matrix equation. These values are standard nomenclature for variables of a polynomial with a single variable x, and as aforesaid, can provide the position of any point along the surface defined in the area between intersection points 82a–82d.

Then, in step 120, the three-dimensional parameters obtained in step 118 are stored in RAM 44, that is, for the area bounded by intersection points 82a-82d. Then, the process continues to step 122 where the next right-most pixel in the row is selected and the process returns back to step 108.

When the last pixel in a row is detected in step 110, the process moves to step 124, where it is detected whether the next pixel is at the end of the image. If not, the process moves to step 126 where the pixel in the first column of the next row is selected, whereupon the process moves back to step 108. If the end of the image is detected in step 124, the process stops at step 126. At this time, each four pixel area of intersection points on face 14a is reconstructed three-dimensionally and stored in RAM 44, that is, there is a three-dimensional reconstruction of the entire face 14a of the patient.

At this time, the three-dimensional information stored in RAM 44 can be stored, for example, on a disk in disk storage 130 associated with CPU 38 and/or a hard copy can be printed out by printer 132. In addition, a three-dimensional mapping of the patient's face 14a can be displayed on a graphics monitor 134 using conventional graphics software, as shown in FIG. 7.

Thus, with the present invention, information relating to swelling of face 14a can be obtained by matching absolute positions of facial surface areas and numerically integrating the volume between the corresponding surface areas. The total swelling volume is computed by summing these volume differences over all corresponding surface areas.

More particularly, using the polynomial of equation (4), the position of any point along the surface defined between intersection points 82a-82d can be obtained. If this same position is obtained before and after swelling of the facial surface, a difference in height of the surface at such positions can be obtained. Preferably, the point chosen is at the center of the area defined between intersection points 82a-82d. Therefore, the volumetric difference for such area can be obtained by multiplying the difference in heights before and after swelling, obtained from the position of the center points, multiplied by the area within the square defined by intersection points 82a-82d. As a result, a volumetric difference can be obtained before and after surgery. This process is performed for all of the four intersection point areas within a particular portion of the face, and the volumetric differences are summed to obtain a total volumetric difference, for example, by using equation 7.4.1 at page 290 of the aforementioned book entitled Numerical Methods and reproduced below as equation 6:

$$\int_a^b f(x)dx = h \sum_{i=i}^n f_{i-\frac{1}{2}} \tag{6}$$

where h is the area of each four intersection box and $f_{i\frac{1}{2}}$ the difference in height between a point in each four intersection box before and after surgery.

Thus, by reviewing the numerical data for the face 14a of a patient before and after surgery, information can be obtained regarding swelling of face 14a. This is useful as aforementioned, to determine, for example, which drugs work better to reduce swelling after surgery. In addition, the results can be superimposed on each other in a form of three-dimensional graphs of the swelling information on graphics monitor 134 and can be printed out as a hard copy on printer 132.

For example, with this information, a graphical analysis can be presented of percent swelling or volume changes with respect to time for three different subjects supplied with three different anti-inflammatory drugs, as shown in FIG. 7, to observe the affects of such anti-inflammatory drugs on a patient. In addition, to verify the results of the invention, the face 14a of the patient can be reconstructed from the data obtained in step 58 of FIG. 3 and displayed on graphics monitor 134, shown in FIG. 8, merely to verify that the operation is functioning correctly.

Having described a specific preferred embodiment of the invention with reference to the accompanying drawings, it will be appreciated that the present invention is not limited to that precise embodiment, and that various changes and modifications can be effected therein by one of ordinary skill in the art without departing from the spirit or scope of the invention as defined in the appended claims.

What is claimed is:

1. A method of optically mapping a three-dimensional surface, comprising the steps of:
    (a) illuminating the surface through a grid structure to produce a grid representation on the surface, said grid representation having intersection points;
    (b) viewing the illuminated surface with a video camera;
    (c) producing a video signal in response to said step of viewing;
    (d) converting said video signal to digital form;
    (e) storing a frame of said digitized video signal in a frame memory;
    (f) defining the grid representation on the surface, from, said stored video signal;
    (g) locating coordinates of said intersection points of said grid representation;
    (h) determining curvatures of said grid representation at said located intersection points; and
    (i) three-dimensionally reconstructing the surface from said coordinates and curvatures of said intersection points.

2. A method of optically mapping a three-dimensional surface, comprising the steps of:
    a) illuminating the surface through a grid structure to produce a grid representation on the surface, said grid representation having intersection points;
    b) viewing the illuminated surface with a video camera;
    c) producing a video signal in response to said step of viewing;
    d) converting said video signal to digital form;
    e) storing a frame of said digitized video signal in a frame memory;
    f) defining the grid representation on the surface, from said stored video signal, said step of defining including the steps of:
        (i) constructing an imaginary box of m x n pixels around substantially each pixel of said stored video signal;
        (ii) determining the value of light intensity of each pixel in each said imaginary box;
        (iii) averaging the values of light intensity in each said imaginary box to produce a local median intensity value for each box; and
        (iv) subtracting the local median intensity value in each body from the pixel about which the body was constructed, to thereby define the grid representation on the surface, from the stored video signal;

(g) locating coordinates of said intersection points of said grid representation;
(h) determining curvatures of said grid representation at said located intersection points; and
(i) three-dimensionally reconstructing the surface from said coordinates and curvatures of said intersection points.

3. A method of optically mapping a three-dimensional surface, comprising the steps of:
(a) illuminating the surface through a grid structure to produce a grid representation on the surface, said grid representation having intersection points;
(b) viewing the illuminated surface with a video camera;
(c) producing a video signal in response to said step of viewing;
(d) storing a frame of said digitized video signal in a frame memory;
(f) defining the grid representation on the surface, from said stored video signal;
(g) locating coordinates of said intersection points of said grid representation, said step of locating coordinates of said intersection points of said grid representation, including the steps of:
  (i) constructing an imaginary box of m x n pixels around substantially each pixel of said grid representation;
  (ii) determining values for each pixel in said imaginary box;
  (iii) defining a pattern of values for an imaginary box of m x n pixels situated around an intersection point;
  (iv) comparing values of the pixels in said constructed imaginary box with the values of the pixels in said defined pattern to determine which pixels are intersection points; and
  (v) assigning coordinates to said pixels determined to be intersection points of said grid representation;
(h) determining curvatures of said grid representation at said located intersection points; and
(i) three-dimensionally reconstructing the surface from said coordinates and curvatures of said intersection points.

4. A method of optically mapping a three-dimensional surface, comprising the steps of:
(a) illuminating the surface through a grid structure to produce a grid representation on the surface, said grid representation having intersection points;
(b) viewing the illuminated surface with a video camera;
(c) producing a video signal in response to said step of viewing;
(d) converting said video signal to digital form;
(e) storing a frame of said digitized video signal in a frame memory;
(f) defining the grid representation on the surface, from said stored video signal;
(g) locating coordinates of said intersection points of said grid representation;
(h) determining curvatures of said grid representation at said located intersection points, said step of determining curvatures of said grid representation of said located intersection points, including the steps of:
  (i) constructing an imaginary box of m x n pixels around each located intersection point of said grid representation; and
  (ii) determining the curvatures of each said intersection point from the pixels of said grid representation in the respective imaginary box of m x n pixels by numerically approximately second derivaturs at said intersection point; and
(i) three-dimensionally reconstructing the surface from said coordinates and curvatures of said intersection points.

5. A method according to claim 1; wherein said video signal is produced at a first time period; and further including the steps of viewing the illuminated surface with a video camera and producing a video signal in response to said step of viewing at a second time period, and repeating steps (d)–(i) for the video signal produced at said second time period, and comparing the three-dimensionally reconstructed surfaces obtained from said video signals at said first and second time periods.

6. Apparatus for optically mapping a three-dimensional surface, comprising:
(a) a grid structure;
(b) illumination means for illuminating the surface through the grid structure to produce a grid representation on the surface, said grid representation having intersection points;
video camera means for viewing the illuminated surface sand for producing a video signal in response thereto;
(d) analog-to-digital converting means for converting said video signal to digital form;
(e) memory means for storing a frame of said digitized video signal in a frame memory; and
(f) central processing means for
  (i) defining the grid representation on the surface, from said stored video signal,
  (ii) locating coordinates of said intersection points of said grid representation,
  (iii) determining curvatures of said grid representation at said located intersection points, and
  (iv) three-three-dimensionally reconstructing the surface from said coordinates and curvatures of said intersection points.

* * * * *